United States Patent [19]
McDonough

[11] Patent Number: 5,242,375
[45] Date of Patent: Sep. 7, 1993

[54] INFANT INCUBATOR AND HUMIDIFIER

[75] Inventor: Robert M. McDonough, Hatfield, Pa.

[73] Assignee: Air-Shields, Inc., Hatboro, Pa.

[21] Appl. No.: 842,455

[22] Filed: Feb. 27, 1992

[51] Int. Cl.⁵ .......................... A61G 11/00
[52] U.S. Cl. ........................................ 600/22
[58] Field of Search ...................... 600/21-22; 5/603, 655

[56] References Cited
U.S. PATENT DOCUMENTS

| | | | |
|---|---|---|---|
| 2,633,842 | 4/1953 | Higgs | 600/22 |
| 2,648,327 | 8/1953 | Gibbon | 600/22 |
| 2,708,927 | 5/1955 | Dixon et al. | 600/22 |
| 3,076,451 | 2/1963 | Stoner | 600/22 |
| 3,821,947 | 7/1974 | Schossow | 600/22 |
| 4,572,427 | 2/1986 | Selfridge et al. | |
| 4,701,415 | 10/1987 | Dutton et al. | |
| 4,796,605 | 1/1989 | Sasaki et al. | |

OTHER PUBLICATIONS

Sunbeam Warm Mist Humidifier Model 1383, 1383-1.
Instruction Manual, Northern Electric Company, 1989.
Dräger Incubator 8000 Brochure.

Primary Examiner—Lee S. Cohen
Assistant Examiner—J. P. Lacyk
Attorney, Agent, or Firm—Ratner & Prestia

[57] ABSTRACT

An infant incubator having a humidifier in which water, used to humidify the air circulated to the hood of the incubator, is supplied to a shallow, heated evaporation tray from a larger unheated water reservoir in regulated amounts. The humidifier is located in the base of the incubator and is arranged such that the reservoir, which is removably carried by a pivotally mounted door, and the evaporation tray, which is slidable into and from the humidifier when the humidifier door is open, can be easily removed for refilling of the reservoir and cleaning or maintenance of the water reservoir, the evaporation tray and other components of the humidifier.

14 Claims, 4 Drawing Sheets

INFANT INCUBATOR AND HUMIDIFIER

BACKGROUND OF THE INVENTION

The present invention relates, in general, to infant incubators and, in particular, to a humidifier for humidifying the air supplied to an infant being maintained and treated in an infant incubator.

As part of the maintenance and treatment of an infant in an incubator, the air supplied to the infant is humidified. Typically, infant incubators have built-in humidifiers through which filtered inlet air is passed. In addition, external humidifiers, which introduce filtered humidified air directly into the hood of the incubator, are available.

For those humidifiers which are part of the infant incubator, many different arrangements for humidifying the circulating air have been suggested or put into actual practice in the past. For example, infant incubators are available in which the water for humidifying the circulating air is held in a heated reservoir within the base of the incubator and the circulating air which is to be humidified is passed over the reservoir. Generally, those infant incubators which are in use today, with humidifiers arranged this way, have one or both of the following shortcomings. First, with the reservoir sized to accommodate enough water to avoid frequent refilling, the entire volume of water in the reservoir is heated to and maintained at the desired temperature, so that establishing, maintaining and changing the desired water temperature are more difficult than for lesser volumes of water. Second, the humidifiers are located within the base of the incubator at points which make difficult refilling the reservoir or removing the humidifier for cleaning or maintenance.

In the humidifier of the Incubator 8000 currently offered by Drager, water is supplied from three unheated bottles to a small, heated cup over which the circulating air is passed for humidification. The amount of water in the three unheated bottles is enough for twenty-four hours of typical humidifier operation.

The humidifier of the Drager Incubator 8000, however, is not arranged for convenient cleaning or replacement of the smaller, heated cup where humidification takes place. In this respect, the humidifier of the Drager Incubator 8000 suffers from the same shortcoming of humidifiers in many infant incubators which are currently available or have been suggested in the past.

In U.S. Pat. No. 4,796,605 to Sasaki et al., a humidifying tank unit 68, having a water tank 81, is arranged for removal from its operating position within the infant incubator through the front of the incubator. The water tank is not heated directly. As heated air passes over the water tank, the air is humidified.

SUMMARY OF THE INVENTION

An infant incubator humidifier, constructed in accordance with the present invention, includes a housing having an opening and a door pivotally mounted to the housing for closing off the opening in the housing. Also included in this infant incubator humidifier is a water reservoir removably carried by the door and movable with the door between a position within the housing when the housing door is closed and a position outside the housing when the housing door is open. This infant incubator humidifier also includes an evaporation tray movable when the housing door is open from a position within the humidifier through the opening in the housing to a position outside the humidifier and having a volume substantially less than the volume of the water reservoir. An infant incubator humidifier, constructed in accordance with the present invention, further includes means for conducting water from the water reservoir to the evaporation tray in regulated amounts and means for heating the evaporation tray.

The infant incubator humidifier of the present invention is part of the air conditioning means located in the base of an incubator. The hood of the incubator is mounted on the base. The infant support of the incubator also is mounted on the base and is enclosed by the hood. The air conditioning means develop conditioned air and circulate conditioned air from the base into the hood and return air from the hood to base. The housing of the humidifier is fitted in an outside surface of the base of the incubator, so that the water reservoir and the evaporation tray can be easily and conveniently removed from or installed in the humidifier.

DETAILED DESCRIPTION OF THE INVENTION

Figure 1:
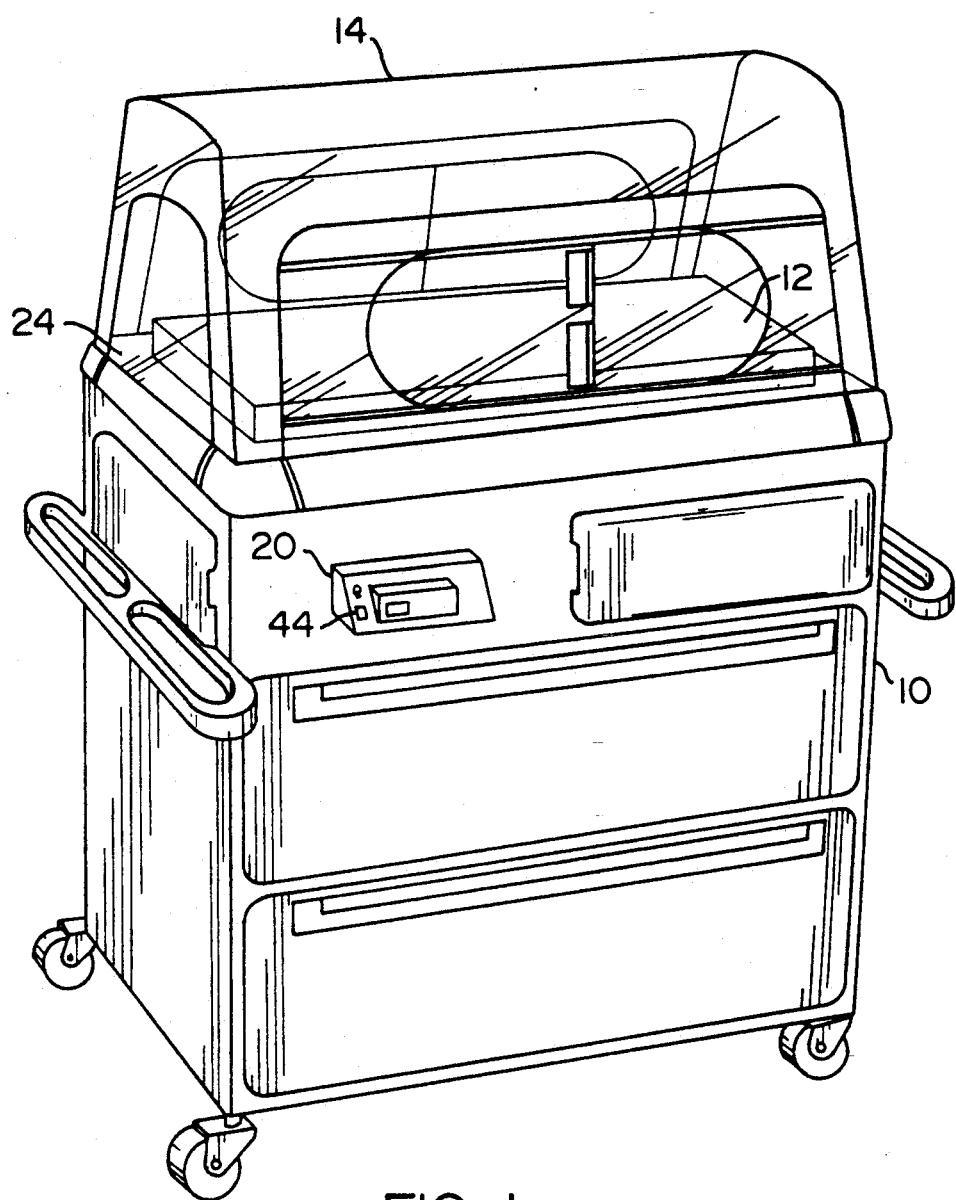
FIG. 1 is a perspective view of an infant incubator constructed in accordance with the present invention in which a humidifier, constructed in accordance with the present invention, is incorporated.
Figure 2:
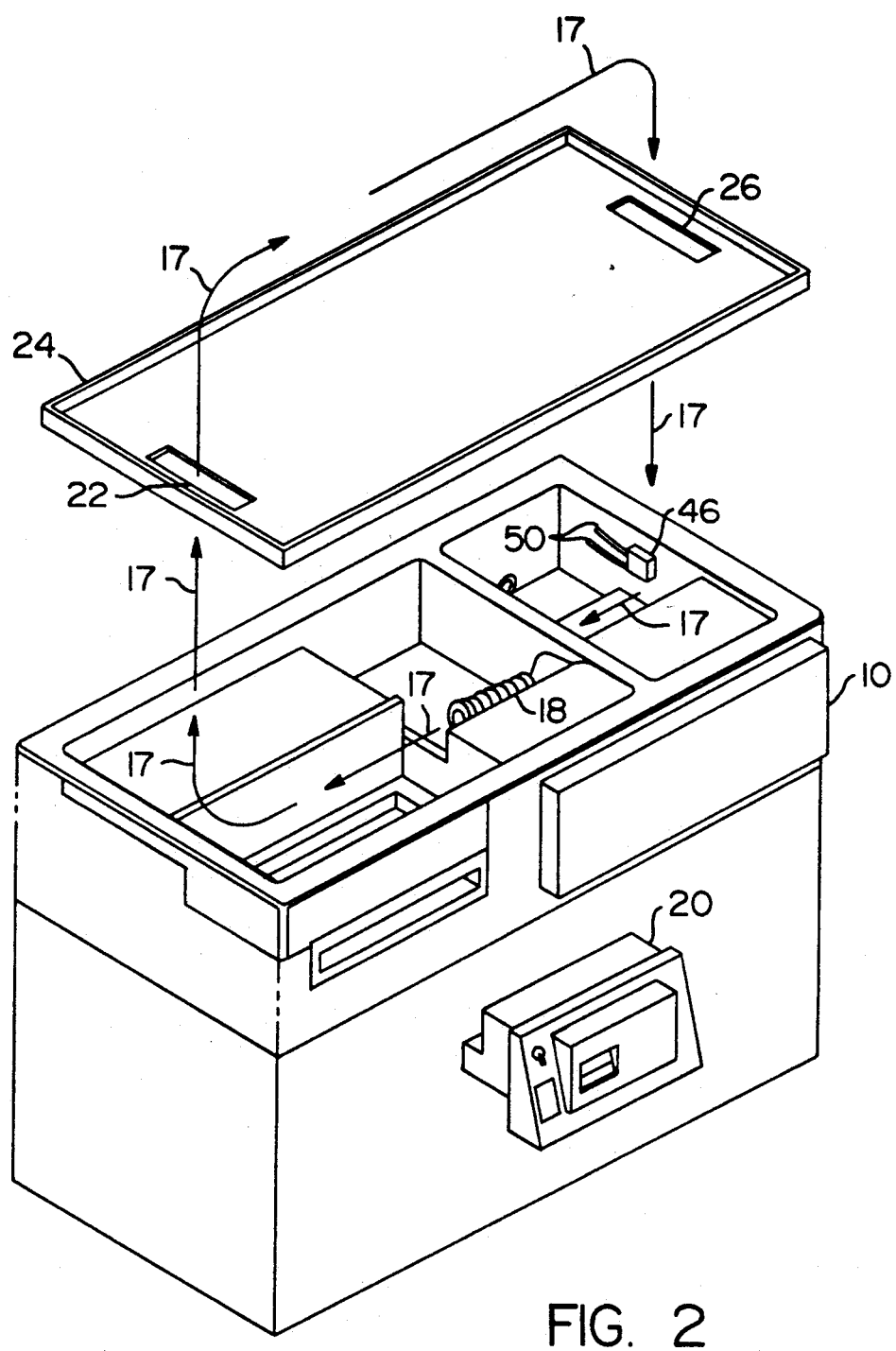
FIG. 2 is an exploded perspective view of a portion of the base of the FIG. 1 infant incubator.

Referring to FIGS. 1 and 2, an infant incubator, constructed in accordance with the present invention, includes a base 10 having an infant support 12 and a hood 14 mounted on base 10 and adapted to enclose infant support 12. Also included in the infant incubator are air conditioning means for developing conditioned air within base 10 and below infant support 12 and for circulating the conditioned air from below the infant support into hood 14 and returning air from the hood to below the infant support. After inlet air from the atmosphere is filtered, this air passes over a heater 18 and through a humidifier 20, to be described in greater detail hereinafter, so that conditioned air, heated and humidified to the desired levels, is introduced into the hood space through an opening 22 in a deck 24 upon which infant support 12 rests. Air is returned from hood 14 to below infant support 12 through an opening 26 in deck 24. If desired, the recirculating air can be filtered prior to passing over heater 18. The flow path for the air circulating in the infant incubator is indicated by the arrows in FIG. 2 which are identified by reference numerals 17. For additional details on an infant support which can be used in the present invention and the apparatus for developing and circulating conditioned air which can be used in the present invention, reference is made to U.S. Pat. No. 3,335,713 to Grosholz et al. which is incorporated herein by reference to supplement the disclosure of various components of an infant incubator.

Figure 3:
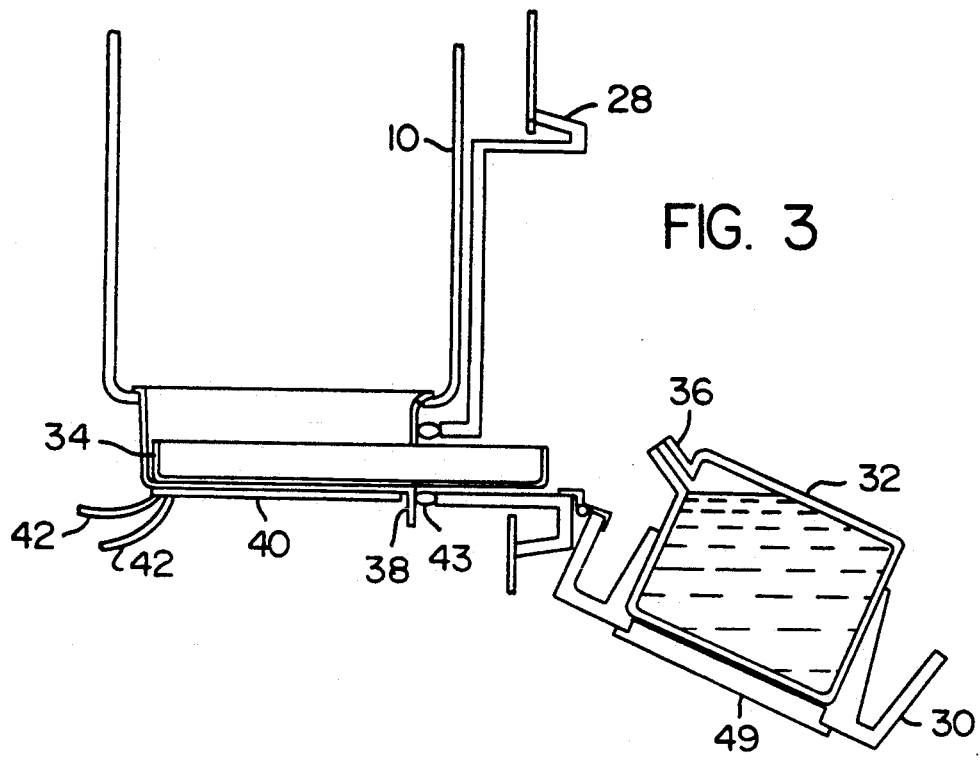
FIGS. 3 and 4 are sectional views of a portion of the FIG. 1 infant incubator with the housing door of the humidifier opened and closed, respectively.
Figure 4:
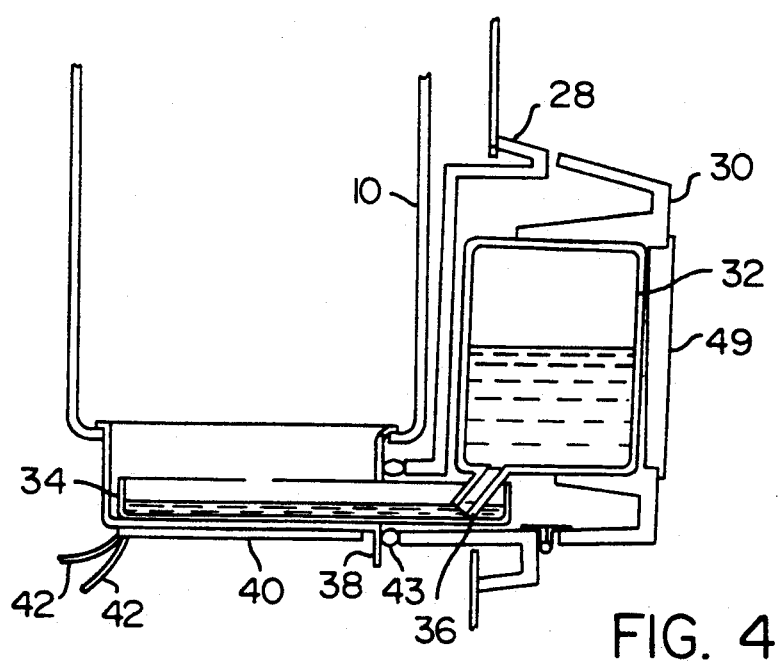
Figure 5:
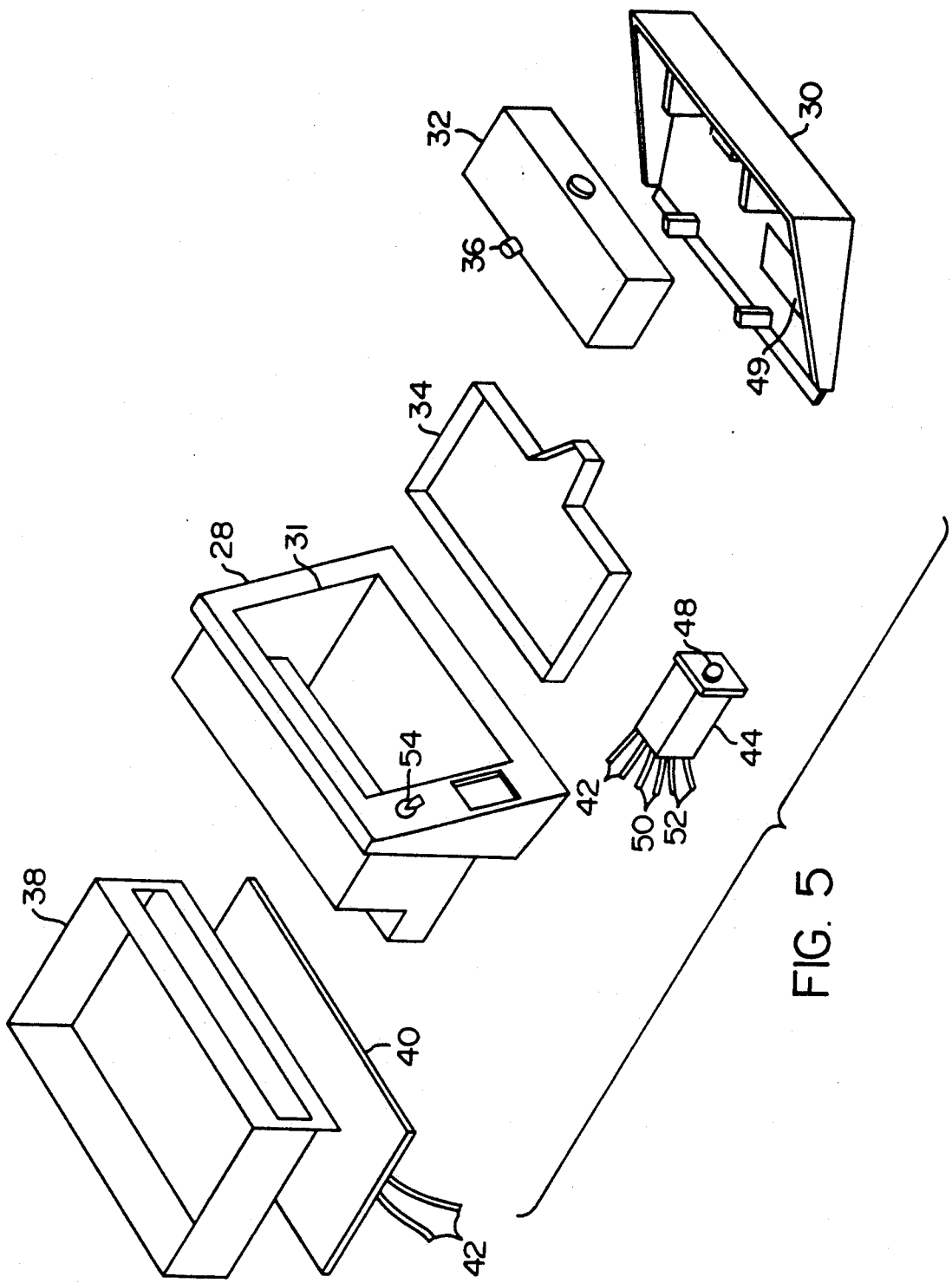
FIG. 5 is an exploded perspective view of an infant incubator humidifier constructed in accordance with the present invention.

As shown in greater detail in FIGS. 3, 4 and 5, humidifier 20, constructed in accordance with the present invention, includes a housing 28 having a pivotally mounted door 30 which closes off an opening 31 in the housing when the door is closed. Housing 28 is fitted in an outside surface of incubator base 10. Also included in humidifier 20 is a water reservoir 32 which is removably carried by door 30 and movable with door 30 between positions within housing 28, as shown in FIG. 4, and outside housing 28, as shown in FIG. 3.

Humidifier 20 further includes an evaporation tray 34 which also is movable from within the humidifier through opening 31 to outside the humidifier. Evaporation tray 34 is relatively shallow and has a volume substantially less than the volume of water reservoir 32. The significance of the volume relationship between water reservoir 32 and evaporation tray 34 will be explained below.

With evaporation tray 34 positioned within the humidifier and water reservoir 32 positioned within housing 28, water is conducted from the water reservoir to the evaporation tray in regulated amounts. For the embodiment of the present invention being described, evaporation tray 34 is below water reservoir 32 when the evaporation tray is within humidifier 20 and water reservoir 32 is within housing 28. Water is conducted from water reservoir 32 to evaporation tray 34 through a water flow passage 36 which extends from the water reservoir into the evaporation tray. Water is conducted from water reservoir 32 until the water level in evaporation tray 34 rises to close off water flow passage 36. As water in evaporation tray 34 evaporates, more water is supplied from water reservoir 32 until the water level in evaporation tray 34 again rises to close off water flow passage 36.

Humidifier 20 also includes means for heating evaporation tray 34. Such means include, for the embodiment of the invention being described, a heater tray 38 and a flat heater 40 which is located beneath evaporation tray 34 and the heater tray and is powered through a pair of leads 42. When the humidifier is operative, evaporation tray 34 is positioned within heater tray 38, so that water in the evaporation tray is heated to humidify the air passing through the humidifier. Heater tray 38 is so positioned relative to housing 28 that evaporation tray 34 moves through opening 31 of the housing when moved from outside the humidifier to within the humidifier and from within the humidifier to outside the humidifier. Flat heater 40 has an area substantially equal to the area of evaporation tray 34. This relationship between evaporation tray 34 and flat heater 40 results in quick heating of the water in the evaporation tray and efficient evaporation. As shown in FIGS. 3 and 4, a gasket 43 is positioned between housing 28 and the front face of heater tray 38 to seal evaporation tray 34 from the outside environment.

The electrical power supplied to heater 40 is controlled by a controller 44 mounted to housing 28 and responsive to a humidity sensor 46, located within base 10 as shown in FIG. 2, and the setting of a knob 48 on controller 44. The setting of knob 48 corresponds to the desired level of humidity. Signals developed by sensor 46 which are indicative of the humidity developed by the humidifier are conducted to controller 44 by leads 50. Leads 52 from controller 44 are connected to the humidifier power control switch 54 by means of which electrical power, conducted to heater 40 by leads 42, is controlled.

Door 30 has a window 49 through which the water level in water reservoir 32 can be seen. Water reservoir 32 and evaporation tray 34 can be autoclavable or disposable.

By the arrangement just described, the smaller amount of water in evaporation tray 34 is heated rather than the larger amount of water in water reservoir 32. As a result, establishing, maintaining and changing the desired water temperature is more efficient than when heating a larger volume of water as is present in the water reservoir. Also, the humidifier is located within the base of the incubator at a point which makes it easy to refill the water reservoir or remove the evaporation tray for cleaning or replacement without disturbing the infant. The location of the humidifier also facilitates removal of the humidifier or the humidifier components for cleaning or maintenance.

While in the foregoing there have been described preferred embodiments of the present invention, it should be understood by those skilled in the art that various modifications and changes can be made without departing from the true spirit and scope of the present invention.

What is claimed is:

1. An infant incubator humidifier comprising:

a housing having an opening;

a housing door pivotally mounted to said housing for closing off said opening in said housing;

a water reservoir removably mounted on said housing door and moved with said housing door between a position within said housing when said housing door is closed and a position outside said housing when said housing door is open;

an evaporation tray movable when said housing door is open from a position within said humidifier through said opening in said housing to a position outside said humidifier and having a volume substantially less than the volume of said water reservoir;

means for conducting water from said water reservoir to said evaporation tray in regulated amounts;

and means for heating said evaporation tray.

2. An infant incubator humidifier according to claim 1 wherein said heating means include a heater tray within which said evaporation tray is positioned when said evaporation tray is within said humidifier.

3. An infant incubator humidifier according to claim 2 wherein said heater tray is so positioned relative to said housing that said evaporation tray moves through said opening in said housing when moved from outside said humidifier to within said humidifier and moved from within said humidifier to outside said humidifier.

4. An infant incubator humidifier according to claim 3 wherein said evaporation tray is below said water reservoir when said evaporation tray is within said humidifier and said water reservoir is within said housing and said water conducting means include a water flow passage extending from said water reservoir into said evaporation tray.

5. An infant incubator humidifier according to claim 4 wherein said heating means further include:

(a) a sensor for generating an indication of the humidity developed by said humidifier, (b) means for setting a desired level of humidity, (c) a heater, and (d) means responsive to said sensor and said setting means for controlling electrical power supplied to said heater.

6. An infant incubator humidifier according to claim 5 wherein said heater is flat and has an area substantially equal to the area of said evaporation tray.

7. An infant incubator humidifier according to claim 6 wherein said flat heater is located beneath said evaporation tray.

8. An infant incubator comprising:
a base having an infant support;
a hood mounted on said base and adapted to enclose said infant support;
and air conditioning means for developing conditioned air within said base and below said infant support and for circulating conditioned air from below said infant support into said hood and returning air from said hood to below said infant support, said air conditioning means including a humidifier having:
(a) a housing fitted in an outside surface of said base and having an opening,
(b) a housing door pivotally mounted to said housing for closing off said opening in said housing;
(c) a water reservoir removably mounted on said housing door and moved with said housing door between a position within said housing when said housing door is closed and a position outside said housing when said housing door is open,
(d) an evaporation tray movable when said housing door is open from a position within said humidifier through said opening in said housing to a position outside said humidifier and having a volume substantially less than the volume of said water reservoir,
(e) means for conducting water from said water reservoir to said evaporation tray in regulated amounts, and
(f) means for heating said evaporation tray.

9. An infant incubator according to claim 8 wherein said heating means include a heater tray within which said evaporation tray is positioned when said evaporation tray is within said humidifier.

10. An infant incubator according to claim 9 wherein said heater tray is so positioned relative to said housing that said evaporation tray moves through said opening in said housing when moved from outside said humidifier to within said humidifier and moved from within said humidifier to outside said humidifier.

11. An infant incubator according to claim 10 wherein said evaporation tray is below said water reservoir when said evaporation tray is within said humidifier and said water reservoir is within said housing and said water conducting means include a water flow passage extending from said water reservoir into said evaporation tray.

12. An infant incubator according to claim 11 wherein said heating means further include:
(a) a sensor for generating an indication of the humidity developed by said humidifier,
(b) means for setting a desired level of humidity,
(c) a heater, and
(d) means responsive to said sensor and said setting means for controlling electrical power supplied to said heater.

13. An infant incubator according to claim 12 wherein said heater is flat and has an area substantially equal to the area of said evaporation tray.

14. An infant incubator according to claim 13 wherein said flat heater is located beneath said evaporation tray.

* * * * *